(12) United States Patent
Weckström

(10) Patent No.: US 6,791,689 B1
(45) Date of Patent: Sep. 14, 2004

(54) SENSOR ASSEMBLY AND METHOD FOR MEASURING NITROGEN DIOXIDE

(75) Inventor: Kurt P. Weckström, Helsinki (FI)

(73) Assignee: Instrumentarium Corp., Helsinki (FI)

(*) Notice: Subject to any disclaimer, the term of this patent is extended or adjusted under 35 U.S.C. 154(b) by 241 days.

(21) Appl. No.: 09/676,107

(22) Filed: Sep. 29, 2000

Related U.S. Application Data

(63) Continuation-in-part of application No. 09/059,805, filed on Apr. 14, 1998, now abandoned.

(51) Int. Cl.$^7$ .............................................. G01N 21/61
(52) U.S. Cl. ..................................................... 356/437
(58) Field of Search ................................. 356/432–439

(56) References Cited

U.S. PATENT DOCUMENTS

| | | | |
|---|---|---|---|
| 3,792,272 A | * | 2/1974 | Harte et al. .................. 250/343 |
| 3,835,322 A | | 9/1974 | Komatsu |
| 3,935,463 A | | 1/1976 | Jacobsen |
| 3,970,430 A | * | 7/1976 | Reader et al. .............. 436/116 |
| 4,023,587 A | | 5/1977 | Dobritz |
| 4,050,823 A | | 9/1977 | Frankenberger |
| 4,067,320 A | | 1/1978 | Olsson et al. |
| 4,225,245 A | | 9/1980 | Roiret et al. |
| 4,637,729 A | * | 1/1987 | Schoch ........................ 356/410 |
| 4,692,621 A | * | 9/1987 | Passaro et al. .............. 250/343 |
| 4,857,735 A | | 8/1989 | Noller |
| 5,299,568 A | | 4/1994 | Forare et al. |
| 5,315,376 A | | 5/1994 | Wada et al. |
| 5,739,038 A | | 4/1998 | Burrows |
| 5,818,598 A | | 10/1998 | Kebabian |

FOREIGN PATENT DOCUMENTS

| | | |
|---|---|---|
| DE | 35 03 720 | 8/1986 |
| EP | 589751 | 9/1993 |
| EP | 660091 | 12/1994 |
| EP | 806216 | 3/1997 |
| GB | 2303447 | 2/1997 |
| JP | 54-21896 | 2/1979 |
| WO | 99/53297 | 10/1999 |

OTHER PUBLICATIONS

UV/Blue Silicon Photodiodes, Mechanical Details Sheet, United Detector Technology, Hawthorne, CA, not dated.

Emerging Technologies—*Nitric Oxide: Delivery, Measurement, and Clinical Application*, S. C. Body et al., Journal of Cardiothoracic and Vascular Anesthesia, vol. 9, No. 6 (Dec.), 1995; pp 748–763.

*Separation of the Absorption Spectra of $NO_2$ and $N_2O_4$ in the Range of 2400–5000A*, T. C. Hall, Jr. et al., The Journal of Chemical Physics, vol. 20, No. 11, Nov. 1952, pp. 1745–1749.

* cited by examiner

*Primary Examiner*—Richard A. Rosenberger
(74) *Attorney, Agent, or Firm*—Andrus, Sceales, Starke & Sawall, LLP

(57) ABSTRACT

A sensing apparatus and method for use in the optical absorption analysis of the $NO_2$ content of a gas sample. The apparatus and method employ radiation from a semiconductor radiation source. The emission spectrum of the radiation has a maximum wavelength of about 600 nm, preferably 380–520 nm. The radiation is passed through the gas sample and sensed by a detector to provide an output signal indicative of the $NO_2$ content of the gas sample. A pair of alternately energized radiation sources may also be used. The sensor apparatus and method may be employed in conjunction with other gas sensing apparatus and methods, such as IR $CO_2$ measurement or NO sensing.

65 Claims, 4 Drawing Sheets

SENSOR ASSEMBLY AND METHOD FOR MEASURING NITROGEN DIOXIDE

CROSS REFERENCE TO RELATED APPLICATIONS

The present application is a continuation-in-part application of U.S. patent application, Ser. No. 09/059,805 filed Apr. 14, 1998, now abandoned.

BACKGROUND OF THE INVENTION

The present invention relates to a sensor assembly and method used for analysis of nitrogen dioxide. The sensor assembly includes a light emitting diode as radiation source, a sample chamber containing the gas to be measured, and at least one radiation detector located to receive the radiation emitted by the radiation source and passed through the gas to be measured. The invention also relates to the analysis of gases containing nitrogen dioxide and/or nitric oxide.

The analysis of small concentrations of nitrogen dioxide ($NO_2$) is typically measured using a sensor for nitric oxide (NO) based on chemiluminescence. The procedure is first to measure the background concentration of NO and then to convert all $NO_2$ to NO in an oven and after that remeasure the NO content. The difference between the two readings gives an estimation of the concentration of nitrogen dioxide. The method is sensitive to below ppm levels but the measurement cannot be performed reliably in real-time especially if the NO background level changes. This is the case when measuring NO delivered to a patient or when measuring the endogenic NO concentration produced in a patient.

Nitrogen dioxide is a highly toxic gas often produced from NO in the presence of oxygen. As a precaution, it has therefore been proposed to monitor inhaled $NO_2$ concentrations to prevent damage to the patient. It is advisable to measure the $NO_2$ concentration on a breath-to-breath basis, meaning that a response time of about 200 ms is required. This is difficult to meet using a $NO_2$ to NO converter.

The same applies for the commonly used electrochemical sensor. It is small and relatively cheap but the response time is too long and the sensitivity low. Such a cell also has a limited lifetime and other gases may interfere with the desired gas measurement. Infrared absorption could also be used to measure $NO_2$ but the sensitivity is low unless the measuring chamber is very long. A long chamber means increased volume and increased response time. Therefore, this method cannot be used clinically. A good review of all mentioned measuring methods is found in S. C. Body et al.: Nitric oxide: Delivery, Measurement, and Clinical Application (Journal of Cardiothoracic and Vascular Anaesthesia, Vol. 9, No. 6, 1995: pages 748–763).

It is well known that nitrogen dioxide is one of the few gases that absorbs light in the visible region, see e.g. the reference T. C. Hall, Jr. and F. E. Blacet: Separation of the Absorption Spectra of $NO_2$ and $N_2O_4$ in the Range of 2400–5000 A (The Journal of Chemical Physics, Vol. 20, No. 11, 1952: pages 1745–1749). To the eye the gas looks brownish in low concentrations. As an aside, it may be noted that this accounts, at least in part, for the brownish color of smog. The gas can even become almost black in high concentrations at elevated temperatures. At room temperature (21° C.) the gas is a mixture of the monomeric $NO_2$ and the dimeric $N_2O_4$ in equilibrium. About 16% is in form of $NO_2$. At 100° C. this fraction has increased to 90% and at about 120° C. practically all molecules are in the monomeric state. Only the monomeric $NO_2$ absorbs visible light above 400 nm so gas temperature is an important parameter unless the isobestic point at about 350 nm, where both types have similar absorption, can be used. The absorption band is broad and almost continuous between about 300 nm and 600 nm with a region of high absorption without disturbance from $N_2O_4$ approximately between 390 nm and 450 nm. The absorption can be measured using either a mercury source with emission lines either at 405 nm or 436 nm or a tungsten lamp filtered to give a wavelength band at the blue end of the spectrum. The problem with these measuring systems is that the source is slow which means that it is not possible to utilize the benefits of a system with high frequency modulation. Therefore, these systems, in addition to being quite bulky, power consuming, and complicated, are not suitable for fast measurements of very low concentrations (<1 ppm) of nitrogen dioxide. In addition, at least the mercury source has limited lifetime.

In U.S. Pat. No. 4,857,735, a spectrophotometer incorporating at least one light emitting diode is presented for conventional measurement of solutions. The absorption is measured through a short cuvette and the reference signal is obtained from measurement of a blank solution. This means that the measurement, in practice, is slow. A high light intensity is essential for measuring solutions with sometimes very high absorbances. Therefore high current pulsing with a small duty cycle is important.

However, for gas measurements there is no need for such intensive pulses because the absorption is always small. The high current would produce excessive current noise which would badly disturb the gas measurement and raise the minimum level of detectable gas concentration. Because of the slow measurement, no means for correction of fast drifts are provided and because of the nature of the measurement no means for compensating changes in source intensity or detector sensitivity are present. The instrument as such would consequently not be suitable for measuring gases such as nitrogen dioxide.

BRIEF SUMMARY OF THE INVENTION

An object of the present invention is to provide a sensor assembly and method for the analysis of nitrogen dioxide with a radiation source efficiently emitting light in the blue end of the visible spectrum. A second object of the invention is to provide a sensor assembly, the source of which is modulatable at a frequency that is high compared to changes measurable e.g. in breathing gas. A third object of the invention is the provision of such a sensor assembly, which is both cheap and simple to construct and long-lasting and thus reliable for monitoring of toxic levels of nitrogen dioxide. A fourth object of the invention is to provide such a sensor assembly, which can measure small concentrations of nitrogen dioxide without interference from other gases, especially nitric oxide. A fifth object of the invention is the provision of such a sensor assembly, which in combination with a sensor for nitric oxide, can measure small concentrations of both nitrogen dioxide and nitric oxide in real time.

A salient feature of the sensor assembly according to the invention is that it can be made small, simple, fast, long-lasting, and reliable. The reason for this is that a light radiating diode is used as light source in the sensor assembly. Blue emitting light emitting diodes, commonly known as LEDs, with high enough optical power and long enough lifetime have not been possible to produce commercially until recently. The emission spectrum of such a light emitting diode fits well to the absorption spectrum of nitrogen dioxide which means that all the benefits of light emitting diodes can be utilized. Since the only gas the sensor assembly reacts to is nitrogen dioxide and since the sensor assembly does not change the composition of the measured gas it is possible to made fast measurements of small concentrations of both nitrogen dioxide and nitric oxide by combining the sensor assembly with a sensitive and fast sensor for nitric oxide, preferably a sensor based on chemiluminescence.

Various other features, objects, and advantages of the invention will be apparent from the following detailed description and the drawings.

BRIEF DESCRIPTION OF THE SEVERAL VIEWS OF THE DRAWING

The invention will be further understood by reference to the following detailed description taken in conjunction with the drawing, in which.

DETAILED DESCRIPTION OF THE INVENTION

Figure 1:
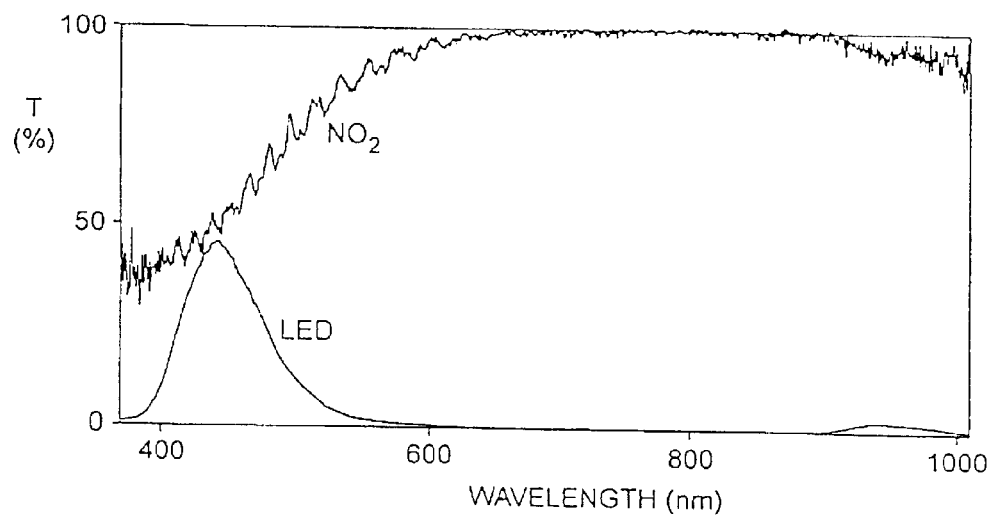
FIG. 1 shows a spectrum of nitrogen dioxide in the visible and near-infrared region together with a typical emission spectrum of a light emitting diode suitable for use in the present invention.

As previously mentioned, nitrogen dioxide ($NO_2$) is one of the few gases that absorbs visible light. The absorption is caused by the complex electronic absorption system $A^2B_1$-$X^2A_1$ with superimposed rotational fine structure. The maximum absorption is approximately at 390 nm, as can be seen in FIG. 1, but the absorption region is broad extending to about 600 nm and even further as a weak absorption. The red end of the spectrum will get more prominent with higher concentration and temperature. For low concentrations only the blue region below about 520 nm shows strong enough absorption to give a reliable measuring result. The concentration of nitrogen dioxide in FIG. 1 was in the range of thousand ppm and the measuring length 100 mm. The absorption of nitrogen dioxide has earlier been used for measuring its concentration mainly for laboratory use. As radiation source a mercury lamp is typically used in order to get enough radiant energy in the blue region. Alternatively, a so called UV-VIS spectrophotometer could be applied to measure the absorption spectrum. For environmental purposes a laser or xenon lamp may be used to spectrally scan long paths of small concentrations of nitrogen dioxide in the air, a method called DOAS (Differential Optical Absorption Spectroscopy). The instruments are typically all slow, bulky, expensive, power consuming and not very sensitive for short measuring distances.

The development of light emitting diodes (LED) has been rapid during the last few years. Until recently it was not possible to manufacture light emitting diodes emitting in the blue region with good enough yield, high enough intensity, and long enough life time. Such a component is now e.g. manufactured by Nichia Chemical Industries Ltd. Of Anan, Japan. The emission spectrum of this LED is also shown in FIG. 1 and it can be seen that the spectral features fit those of nitrogen dioxide absorbance very well. Moreover it is possible to take advantage of several features related to the LED when constructing a gas sensor. The LED is a very fast component meaning that high sampling rates can be used. In this way low frequency noise, so called 1/f noise, can be avoided without slowing down the response time. The LED is a very cheap component and it has a very low power consumption with low voltage as opposed to a mercury lamp. It is small size being a semiconductor chip. Thus it is possible to manufacture a small, cheap and sensitive $NO_2$ sensor with properties surpassing those of earlier measuring devices in many respects.

The preferred radiation source in this invention is a light emitting diode. However, another possible light radiating diode to which considerable development efforts are being devoted is the laser diode. This component resembles a light emitting diode but is equipped with a resonator making laser action possible at currents higher than normally needed for good light output from a light emitting diode. The laser diode within the blue region is still expensive and not very reliable but in the near future the situation will change. The laser light emission from such a laser diode has a very narrow spectral bandwidth compared to the light emission from a light emitting diode. To a slight extent the spectrum of the light emitting diode as shown in FIG. 1 will, however, also be present in the laser diode spectrum and could be used in a manner similar to what is described below for the light emitting diode.

Figure 2:
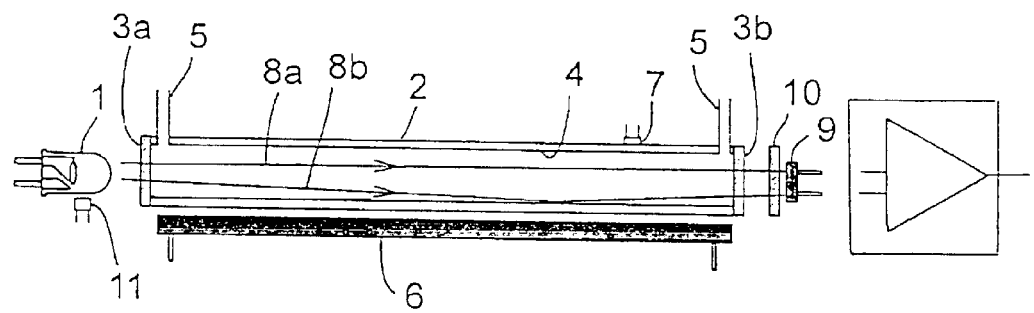
FIG. 2 shows, in longitudinal section, a sensor assembly for nitrogen dioxide according to the invention.

A construction of the sensor assembly is shown in FIG. 2. The radiation source 1 is a light emitting diode emitting in the blue region with maximum radiation between about 380 nm and 520 nm depending on the construction of the diode. The specific LED, the emission spectrum of which is shown in FIG. 1, has its emission maximum at about 450 nm. The LED chip 1 in FIG. 2 is shown in a typical LED case with a reflector and a plastic lens that collimates the radiation. Of course it could be different but the standard package is beneficial because it is efficient and cheap. It could also be replaced by a laser diode.

The gas to be measured is normally confined to a sample chamber 2 which typically is a long tube with two end windows 3a and 3b, reflecting inner walls 4 and gas inlet 5a and outlet 5b. The length of this chamber could be about 100 mm for rapid measurements of a sampled gas. If the intention is to measure e.g. breathing gas, a response time of about 200 ms is required in order to resolve all details of the inspiration and expiration. Of course, the sample chamber could also look different, e.g. be folded using mirrors, or it could even be absent for environmental measurements. For a fast sampling measurement, the sample chamber 2 in FIG. 2 is, however, the simplest. A sample chamber is needed especially if the sample gas is to be measured at a higher temperature than ambient or temperature stabilization is applied. The benefit of a higher measuring temperature is not only to prevent condensation of water on the windows 3 but to get more signal. As pointed out above, more nitrogen dioxide is formed by conversion from the dimeric form $N_2O_4$ as temperature rises until all the oxide is in the monomeric form $NO_2$ at about 120° C. The dimeric form does not absorb in the visible region which means that at higher temperature a deeper absorption and subsequently a better signal and higher sensitivity will result. It is not necessary to heat the sampled gas to 120° C. If heating is applied with a heating element 6 a temperature around 50° C. seems adequate for practical reasons. For less sensitive measurements, where the danger of water condensation is absent, heating can be omitted. However, the temperature of the sampled gas must be measured in order to compensate the measured concentration value. In FIG. 2 this is done using temperature sensor 7, which preferably could be a thermistor or some other semiconductor component. The foregoing temperature dependence can be stored in memory in a control unit and used for compensation of the total nitrogen dioxide gas concentration according to the measured gas temperatures. Other temperature dependencies in the assembly, for example, that of the radiation source and/or that of the detector, may be similarly stored to so as to provide a single temperature dependence function or table for use in the sensor assembly.

The radiation from an LED 1 of the type described above is quite well collimated. Part of the radiation, 8a goes straight through the sample chamber and the rest, 8b, is reflected off the inner wall 4. The radiation is, in other words, efficiently transmitted through the sample chamber to a detector 9. Even if the LED is preferable because of cost reasons, the radiation transfer would be even simpler using a laser diode because of its beam coherence and the subsequent possibility to collimate the beam very accurately. The detector 9 can preferably be a conventional silicon detector or a so called blue enhanced type of detector, such as that made and sold by United Detector Technology of Hawthorne, Calif. Such a component is fast enough to resolve even a high sampling frequency. A sampling frequency of at least about 10 Hz is required for resolving a breathing curve but in this case it is beneficial to work in the kHz range or even higher to avoid 1/f noise. The detector can be connected to a control unit having a narrowband amplifier centered at this high sampling frequency with good signal-to-noise ratio and good stability as a consequence. An optical filter 10 is positioned in front of the detector 9 to prevent ambient light from disturbing the measurement. Of course the sensor assembly should in practice be built into a light tight case. The filter can be a blue color filter or it can be a narrow band Fabry-Perot filter centered at or near the maximum of the spectral radiation of the LED or laser diode. An accurate measurement is also sensitive to changes in the zero signal, i.e. the signal without absorbing gas. Slow changes can be compensated for by occasionally filling the sample chamber with gas free from $NO_2$ and measuring and storing this signal for use as a denominator when calculating the gas transmission. This principle does not work for fast changes or in cases when it is not possible to fill the space between the LED source 1 and the detector 9 with non-absorbing gas. There are a number of conventional ways to compensate for such fast changes. If the main source of changes is the LED itself it may be sufficient to monitor its light output using an optical reference detector 11 near the LED as shown in FIG. 1. The LED of source 1 is normally connected to a constant current source with a modulation option and the detector 11 can be wired to give feedback to this power source to achieve additional optical stabilization. The so called dark signal is registered when the LED source 1 is in its off state and no light is reaching the detector 9. When both the dark level and zero level are known, the real gas absorption can be calculated and the gas concentration found after linearization and calibration of the sensor assembly. A logarithmic linearization curve is almost correct in this case because Lambert-Beer's law is obeyed as opposed to most infrared gas absorption measurements. However, this fact is of minor importance today when microcomputers can handle any measured linearization function.

Figure 3:
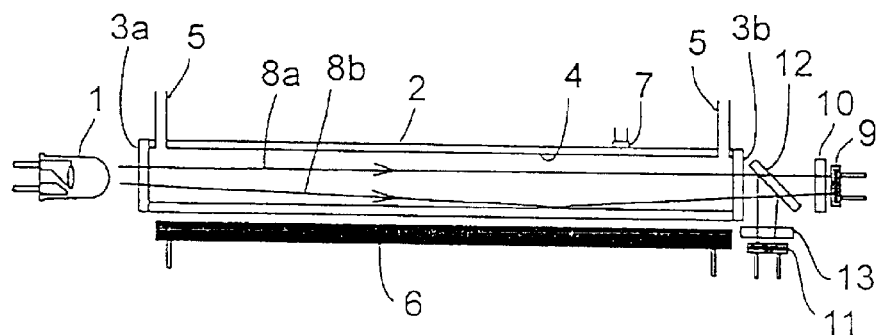
FIG. 3 shows an alternative embodiment of a sensor assembly for nitrogen dioxide according to the invention.

It may not be enough to monitor only changes in the LED as shown in FIG. 2 or only slow changes in the zero signal. Dirt can accumulate on the windows 3 and walls 4 of sample chamber 2. To compensate for such changes, a reference detector 11 may be provided at the other end of the sample chamber 2 as shown in FIG. 3. A beam splitter 12 reflects part of the radiation 8a and 8b on the reference detector 11. An optical filter 13 in front of the detector 11 has the same function as filter 10. However, the wavelength region seen by detector 9 and reference detector 11 must be different so that the signal from reference detector 11 is not sensitive, or is least less sensitive, to the light absorption in nitrogen dioxide. As it is beneficial to use the same source 1 for both detectors, the wavelength region has to be divided. The long wavelength part of the LED emission, in FIG. 1 above about 480 nm, could be used for detection by reference detector 11. To achieve this, either beam splitter 12 can be dichroic with an edge at about 480 nm, or filter 13 can be transmissive for wavelengths above the limit if the beam splitter is conventional. There is still gas absorption in that region but to a smaller extent than at the maximum of the LED emission. In other words, the ratio between the measured signal and the reference signal will react to the absorption of nitrogen dioxide. It is also possible to use the small emission in the near-infrared region about 950 nm shown in FIG. 1 as reference. Also here a slight gas absorption is observed. However, the occurrence and strength of this emission depends on the LED manufacturing process and furthermore this wavelength region does not necessarily reflect the intensity changes at the blue end of the spectrum because of different absorption properties of the possible dirt and a fairly strong wavelength dependence of light scattering.

Figure 4:
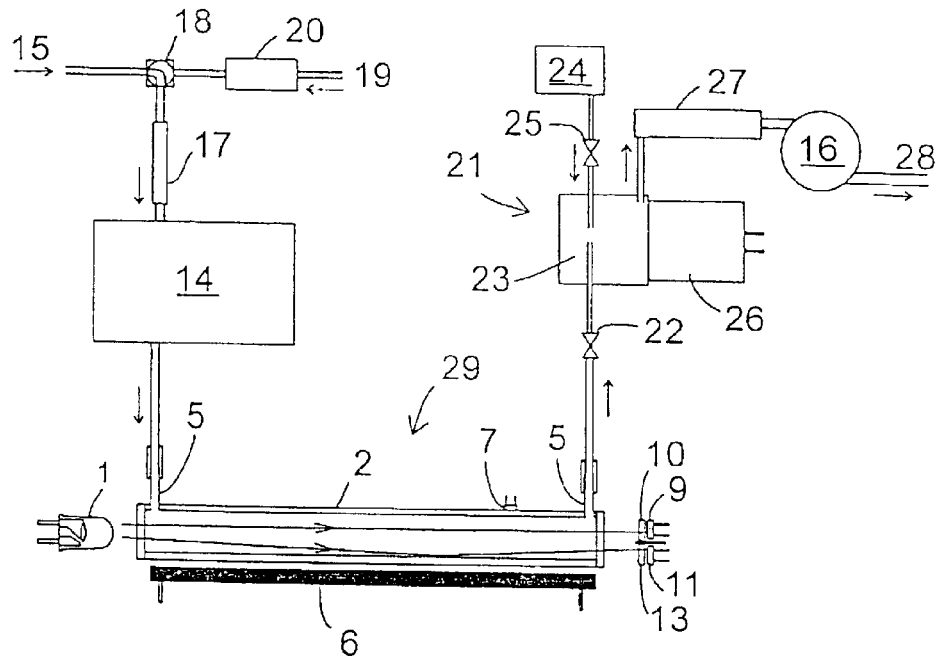
FIG. 4 shows an alternative sensor assembly for nitrogen dioxide according to the invention connected to an infrared sensor and a sensor for nitric oxide.

In FIG. 4 another embodiment of the sensor assembly in FIG. 3 is shown. Here no beam splitter is used and detector 9 with filter 10 and reference detector 11 with filter 13 are both positioned side-by-side and optically shielded from each other. This figure also shows a measuring system for fast measurement of other gases. A measuring system 14 for infrared absorption is connected in series with the $NO_2$ sensor assembly 29. In this way it is possible to measure e.g. carbon dioxide. The sampled gas 15 is drawn into the system using a pump 16. Normally it is not important which sensor is connected nearer to the sampled gas inlet 15 but sometimes, especially in connection with breathing gases, it is necessary to have a fastest possible carbon dioxide signal and this necessitates a position of the corresponding sensor near the sampled gas inlet 15. In the gas stream it is often necessary to have a gas drying system 17 to avoid water condensation and infrared absorption. A simple solution is to connect a Nafion tube in the sampling line. For establishing a zero level a valve 18 can be turned to an inlet of reference gas 19, normally ambient air, with possible scrubber 20 to remove nitrogen dioxide and other disturbing gases, e.g. carbon dioxide $CO_2$ and nitric dioxide NO.

Downstream and after the nitrogen dioxide sensor assembly 29 it is possible to connect a sensor 21 for nitric oxide (NO). It can be a conventional electrochemical cell but if small-concentrations are to be measured with fast response a chemiluminescent sensor is a better choice. Such instruments are e.g. manufactured by Sievers Instruments, Inc. of Boulder, Colo. as product Model 280. These sensors normally consist of a gas flow restricting element 22 to create underpressure in a reaction chamber 23, an ozone generator 24 with its flow restricting element 25 and a sensitive detector 26, normally a photomultiplier tube. The ozone supplied to the chamber 26 reacts with possible nitric oxide in the sampled gas to form nitrogen dioxide in an excited state and the relaxation creates photons that are detected by detector 26 and are related to the concentration of nitric oxide. Since nitrogen dioxide is formed in sensor 21, this sensor has to be downstream from other sensors. Additionally, the ozone component contaminates and dilutes the sample. A scrubber 27 is normally connected in the sampling line after the nitric oxide sensor to remove ozone and other toxic gases before they are pumped out to the outlet 28 of the system.

In principle also small concentrations of nitrogen dioxide can be measured using the chemiluminescent sensor 21 if the $NO_2$ content is first converted to NO by heating. This is the conventional way to measure $NO_2$ but simultaneous fast measurements of both $NO_2$ and NO are not possible to perform. First, the NO content must be measured, then the sum of the $NO_2$ to be measured and converted to NO is measured, and the actual $NO_2$ concentration is obtained by subtraction. Such a measurement is very vulnerable and apt to changes in e.g. the NO concentration. The measurement is in other words not suitable for real time measurement of e.g. breathing gases. The nitrogen dioxide sensor assembly 29, on the contrary, does not alter the measured gas in any way and a possible content of nitric oxide remains intact so that also it can be measured directly using sensor 21.

Figure 5:
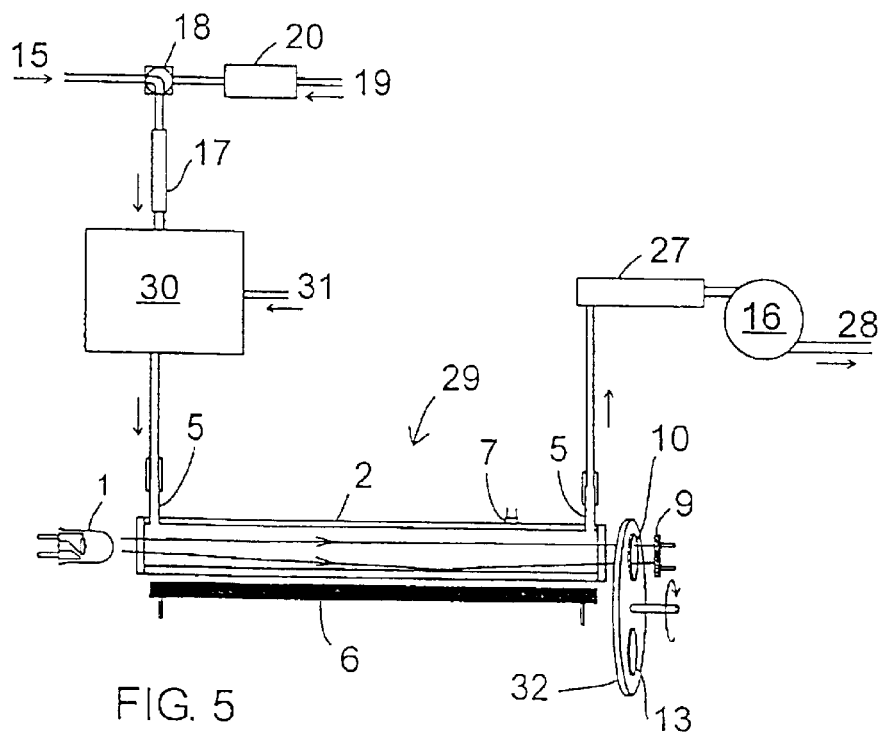
FIG. 5 shows a system with an alternative sensor assembly according to the invention connected to be able to indirectly measure nitric oxide.

In FIG. 5 another alternative construction of the nitrogen dioxide sensor assembly is shown. Only one detector 9 is needed because a revolving filter wheel 32 has been used to alternately position filter 10 and filter 13 in front of the detector 9. In this way any differences in characteristics that would arise when two detectors are used are eliminated. Naturally, the revolving speed of filter wheel 32 must be kept lower than the modulation frequency of the LED.

The system shown in FIG. 5 shows like FIG. 4 another possibility for connecting the nitrogen dioxide sensor assembly 29. In addition to being a cheap and reliable sensor for monitoring toxic levels of nitrogen dioxide, according to FIG. 5, it is even possible to indirectly measure nitric oxide with sensor 29 by first converting the NO content into $NO_2$ in a gas mixer 30 e.g. by letting it mix and react with ozone or oxygen 31. For slow measurements the oxygen in air is adequate for this purpose but for fast measurements ozone can be used. The embodiment of FIG. 5 thus becomes a very cheap and simple way to monitor, especially, relatively high concentrations of NO (normally ppm level to a level of a few decades of ppm) e.g. in a gas container. The $NO_2$ content, if any, in the sample gas 15 can be measured at first and then the NO content can be found out by subtracting this $NO_2$ content from the total amount of $NO_2$ including the converted NO amount, compensated for the added gas flow 31 from the gas mixer 30. The difference is the NO content.

Another possibility would be to use the chemiluminescent NO sensor 21 as the mixer and NO converter instead of mixer 30 shown in FIG. 5 and connect it in front of the $NO_2$ sensor assembly 29. In this way the NO sensor 21 would first measure the NO content in the sampled gas, then rapidly convert it into $NO_2$ which would be measured by the $NO_2$ sensor assembly 29, and the actual $NO_2$ content would be found as the difference between this total $NO_2$ content, compensated for the added ozone gas flow and the $NO_2$ content resulting from NO conversion. However the configuration shown in FIG. 4 gives a more direct measurement and it is therefore deemed more reliable and preferable than the configuration shown in FIG. 5.

Figure 6:
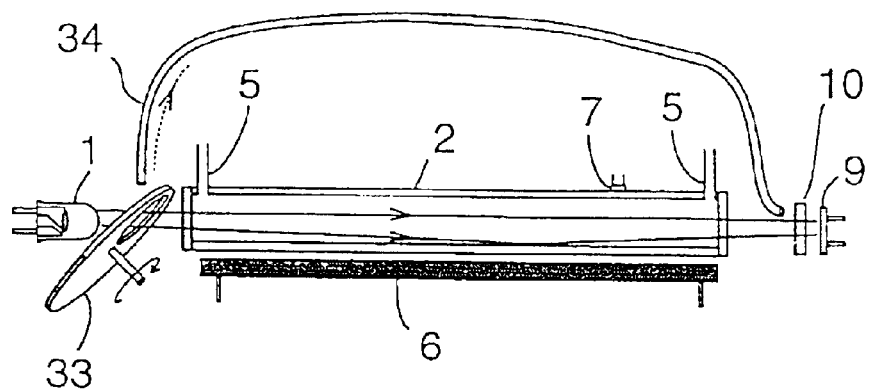
FIGS. 6 and 7 show further embodiments of the sensor assembly according to the invention.
Figure 7:
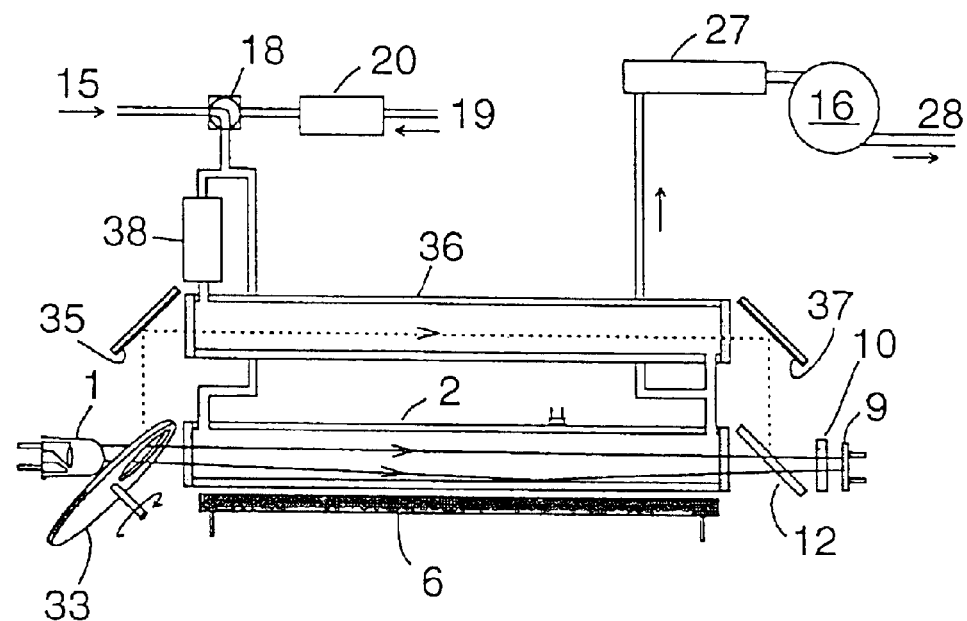

FIGS. 6 and 7 present alternative embodiments of the sensor assembly with only one source 1 and one detector 9. Both have a reflecting chopper wheel 33 with a hole in it so that the radiation either goes straight through the sample chamber 2 or is reflected into an alternative reference path on its way to filter 10 and detector 9. In FIG. 6 the reference path consists of an optical fiber 34 which transfers the radiation to detector 9. Then it is possible to compensate both for fluctuations in the source radiation and changes in detector sensitivity.

If, in addition, it is necessary to compensate for possible disturbing absorption in the sample gas flow or chamber, a reference chamber 36 can be connected to the sample flow in such a way that any $NO_2$ content of the sample gas at inlet 15 is removed using a scrubber 38 shown in FIG. 7. It would also be possible to connect reference chamber 36 to some other usable gas flow or even use it without gas flow, especially if it could be expected that both chambers 2 and 36 behave similarly when it comes to disturbing absorption. The radiation is directed through reference chamber 36 via mirrors 35 and 37 and using a beam splitter 12. Of course, other optical arrangements are also possible.

Figure 8:
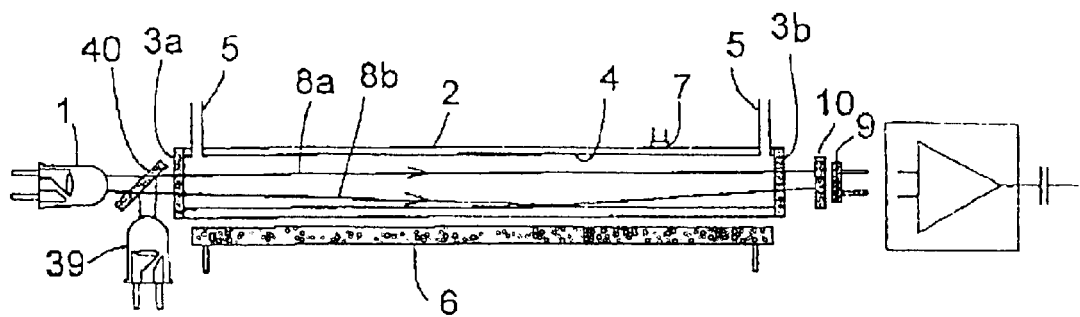
FIG. 8 shows yet another embodiment of the sensor assembly according to the invention.
Figure 9:
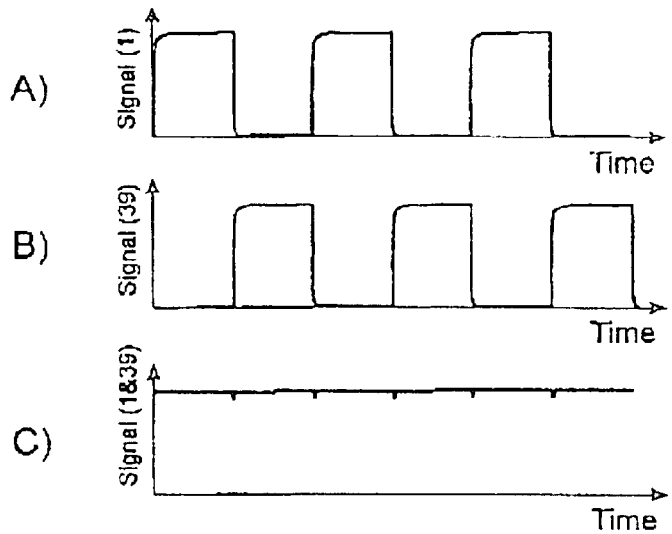
FIGS. 9A, 9B and 9C show operation of the embodiment of the invention shown in FIG. 8 when measurement of nitrogen dioxide is not occurring.
Figure 10:
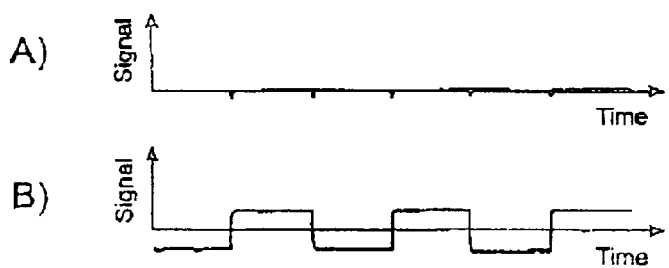
FIGS. 10A and 10B show operation of the embodiment of the invention in FIG. 8 when measurement of nitrogen dioxide is occurring.

FIGS. 8, 9, and 10 show a further embodiment of sensor assembly in which two light sources 1, 39 are used. As shown in FIG. 8, radiation from both light sources may be applied to sample chamber 2 using a beam splitter 40, preferably of the dichroic type. Or, the light sources may be positioned side-by-side to apply radiation to sample chamber 2.

Light source 1 is used for nitrogen dioxide measurement and resembles the light source 1 of above described embodiments. As such, it may be of the semiconductor type, e.g. a light emitting diode, emitting light in the blue region.

Light source 39 may also be of the semiconducting type, such as a light emitting diode. While it is preferable that the operating characteristics of light source 1 and light source 39 be similar, the emitted color spectrum can be different. Thus, light source 39 can emit light in the blue region or in some other color or infrared spectral range. It is preferable to choose the wavelength of the radiation from light source 39 so that the absorption by nitrogen dioxide is as small as possible. If the radiation from light source 39 is in the blue region, it is necessary to use only that part of the emission spectrum in which absorption from nitrogen dioxide is small. This would be the longer wavelength side of the light emitting diode wavelength spectrum shown in FIG. 1. Selection of the appropriate radiation wavelength may be carried out using dichroic beam splitter 40 or a separate radiation filter.

As shown in FIG. 8, a single detector 9, which may be of the type described above, can be used for both light sources 1, 39. Filter 10 in front of detector 9 transmits the radiation from both the light sources and reduces the influence of ambient light. An amplifier is connected to the output of detector 9.

Light sources 1, 39 are alternately energized, as shown in FIGS. 9A and 9B. Thus the operation of the light sources may be described as one in which both sources are chopped at the same frequency, preferably in the kilohertz range, with a duty cycle of close to 50%, and with a phase shift of approximately 180°. When there is no nitrogen dioxide present to be absorbed, the signal from detector 9 produced by the radiation from intermittently and alternately energized light source 1 is shown in FIG. 9A. Under the same conditions, the signal from detector 9 produced by the radiation from intermittently and alternatively energized light source 39 is shown in FIG. 9B.

The composite output of detector 9 is shown in FIG. 9C. The magnitude of the signals from detector 9 produced by light sources 1 and produced by light source 39 is adjusted, as by appropriate bias means in a manner that seeks to provide the same level of detector signal for both light sources so that the composite signal has a constant magnitude, as shown in FIG. 9C. Any small disturbances resulting from the fact that the signals shown in FIGS. 9A and 9B may not be perfectly square can be easily filtered out. By an AC coupling as symbolically shown by the capacitor in FIG. 8, any DC component can be removed so that the zero output signal shown in FIG. 10A can be provided when no nitrogen dioxide is present in sampling chamber 2.

Breathing, or other, gas containing nitrogen dioxide is now admitted to sample chamber 2. The nitrogen dioxide causes absorption of the radiation from light source 1, reducing the output signal from detector 9 during the intermittent and alternating operation of light source 1 from the level shown in FIG. 9A. The nitrogen dioxide causes little or no absorption of the radiation from light source 39, so that the output signal from detector 9 during the intermittent and alternating operation of this light source is essentially the same as is shown in FIG. 9B.

The result of the foregoing is a composite output signal from the sensor assembly that will have a varying component as shown in FIG. 10B, the magnitude of which is indicative of the concentration of nitrogen dioxide in the gas in sample chamber 2. Since the frequency of the output signal from detector 9 is constant at the chopping frequency, the bandwidth of the amplifier may be narrowed to that frequency to increase the sensitivity of the measurement and to reduce noise.

Even though many different possibilities have been shown how to use a fast and simple nitrogen dioxide sensor assembly based on a light radiating diode it is evident that many variations of the sensor assembly and many other applications within this invention are possible to construct.

It is recognized that other equivalents, alternatives, and modifications aside from those expressly stated, are possible and within the scope of the appended claims.

What is claimed is:

1. A sensor assembly for use in a patient breathing system for providing real-time optical absorption analysis of the $NO_2$ content of the breathing gases of the breaths of a subject and providing real time analysis of the NO content of the breathing gases of the breaths of a subject, said sensor assembly comprising:

a semiconductor radiation source emitting radiation having a emission spectrum with a maximum wavelength of about 600 nm, the radiation source being operated at a sampling frequency of at least about 10 Hz;

a sample chamber having an inlet conduit for supplying a flow of breathing gases during the breaths of the subject through the chamber, the radiation from said radiation source passing through the gas in said sample chamber, said sample chamber having an outlet conduit for passing the breathing gases from said sample chamber;

a detector for receiving radiation passed through the breathing gases flowing through in said sample chamber and for providing an output signal indicative of the $NO_2$ content of the breathing gases in said sample chamber, the detector providing the output signal in a response time of about 200 ms, such that the sensor assembly provides the output signal in real-time with respect to the breaths of the subject; and an NO gas sensor coupled to said outlet conduit for providing a real time measurement of the NO content of the breathing gases.

2. A sensor assembly according to claim 1 wherein said semiconductor radiation source is further defined as emitting radiation having an emission spectrum with a maximum wavelength of about 520 nm.

3. A sensor assembly according to claim 1 wherein said semiconductor radiation source emits radiation in an emission spectrum between about 380–520 nm.

4. A sensor assembly according to claim 1 wherein said semiconductor radiation source comprises a light emitting diode.

5. A sensor assembly according to claim 1 wherein said semiconductor radiation source comprises a laser diode.

6. A sensor assembly according to claim 1 further including a further detector for detecting the emitted radiation of said radiation source, said further detector being connected to a power supply for said radiation source for stabilizing the operation of said radiation source.

7. A sensor assembly according to claim 1 wherein said detector comprises a silicon detector.

8. A sensor assembly according to claim 1 wherein said detector comprises a blue enhanced type of detector.

9. A sensor assembly according to claim 1 wherein said detector is coupled to an output signal amplifier.

10. A sensor assembly according to claim 9 wherein said output signal amplifier is a narrow bandwidth amplifier, the bandwidth of which is centered at said sampling frequency.

11. A sensor assembly according to claim 1 further including an optical filter interposed in front of said detector along a path of the emitted radiation in said sensor assembly.

12. A sensor assembly according to claim 11 wherein said optical filter passes a spectral band centered on a maximum of the emission spectrum of said radiation source.

13. A sensor assembly according to claim 1 further including a reference detector for detecting the radiation passed through the breathing gases in said sample chamber and for compensating said first mentioned detector.

14. A sensor assembly according to claim 13 wherein said reference detector includes means for reducing the sensitivity of said reference detector to spectral absorption resulting from the presence of $NO_2$ in the breathing gases.

15. A sensor assembly according to claim 14 wherein said reducing means comprises means for causing a different spectral region of said emission spectrum to be applied to said reference detector than the spectral region of said emission spectrum applied to said first mentioned detector.

16. A sensor assembly according to claim 15 wherein said means applying different spectral regions of said emission spectrum to said first mentioned detector and to said reference detector comprises a dichroic beam splitter interposed in a path of the radiation exiting said sample chamber for applying beams of different spectral regions to said first mentioned detector and said reference detector.

17. A sensor assembly according to claim 15 wherein said means applying different spectral regions of said emission spectrum to said first mentioned detector and to said reference detector comprises filters interposed in front of said first mentioned detector and said reference detector, said filters passing different spectral regions of said emission spectrum to said first mentioned detector and said reference detector.

18. A sensor assembly according to claim 13 wherein said radiation source emits radiation in a further emission spectrum and wherein said reference detector detects radiation in said further emission spectrum.

19. A sensor assembly according to claim 1 further including means having a pair of filters, said filters passing different spectral regions of said emission spectrum and means for placing one or the other of said filters in front of said detector along a path of the radiation in said sensor assembly for providing compensation to said detector.

20. A sensor assembly according to claim 1 further including a temperature sensor for sensing the temperature of the breathing gases in said sampling chamber and means for compensating the output signal of said detector in accordance with the sensed temperature of the breathing gases.

21. A sensor assembly according to claim 20 wherein said sample chamber has a heater operatively associated therewith.

22. A sensor assembly according to claim 1 wherein the sampling frequency of said radiation source is in the kHz range.

23. A sensor assembly according to claim 1 wherein said NO gas sensor comprises a chemiluminescent sensor.

24. A sensor assembly according to claim 1 wherein said NO gas sensor includes an electrochemical cell.

25. A sensor assembly for use in a patient breathing system for providing real-time optical absorption analysis of the $NO_2$ content of the breathing gases of the breaths of a subject, said sensor assembly comprising:

a first semiconductor radiation source emitting radiation having a emission spectrum with a maximum wavelength of about 600 nm;

a sample chamber to which is supplied a flow of breathing gases during the breaths of the subject, the $NO_2$ content of the breathing gases so supplied being measured by said sensor assembly, the radiation from said first radiation source passing through the gas in said sample chamber;

a detector for receiving radiation passed through the breathing gases in said sample chamber; and a second semiconductor radiation source providing radiation for passage through said sample chamber for receipt by said detector, the wavelength of the radiation provided by said second radiation source being such as to minimize absorption of the radiation by nitrogen dioxide, said first and second radiation sources being alternately energized at a sampling frequency;

said detector providing an output signal formed by the alternative energization of said radiation sources indicative of the $NO_2$ content of the breathing gases in said sample chamber in real-time with respect to the breaths of the subject.

26. A sensor assembly according to claim 25 wherein said first semiconductor radiation source is further defined as emitting radiation having an emission spectrum with a maximum wavelength of about 520 nm.

27. A sensor assembly according to claim 25 wherein said first semiconductor radiation source emits radiation in an emission spectrum between about 380–520 nm.

28. A sensor assembly according to claim 25 wherein at least one of said first and second semiconductor radiation sources comprises a light emitting diode.

29. A sensor assembly according to claim 25 wherein at least one of said first and second said semiconductor radiation sources comprises a laser diode.

30. A sensor assembly according to claim 25 further including a further detector for detecting the emitted radiation of at least one of said radiation sources, said further detector being connected to a power supply for said at least one radiation source for stabilizing the operation of said at least one radiation source.

31. A sensor assembly according to claim 25 wherein said detector comprises a silicon detector.

32. A sensor assembly according to claim 25 wherein said detector comprises a blue enhanced type of detector.

33. A sensor assembly according to claim 25 wherein said detector is coupled to an output signal amplifier.

34. A sensor assembly according to claim 33 further including an AC coupling for said amplifier for removing DC components.

35. A sensor assembly according to claim 33 wherein said output signal amplifier is a narrow bandwidth amplifier, the bandwidth of which is centered at said sampling frequency.

36. A sensor assembly according to claim 25 further including a filter interposed in front of said detector along a path of the emitted radiation in said sensor assembly.

37. A sensor assembly according to claim 25 further including a temperature sensor for sensing the temperature of the breathing gases in said sampling chamber and means for compensating the output signal of said detector in accordance with the sensed temperature of the breathing gases.

38. A sensor assembly according to claim 37 wherein said sample chamber has a heater operatively associated therewith.

39. A sensor assembly according to claim 25 wherein each of said radiation sources is energized at a sampling frequency of at least about 10 Hz.

40. A sensor assembly according to claim 39 wherein each of said radiation sources is energized at a sampling frequency in the kHz range.

41. A sensor assembly according to claim 25 further including an NO gas sensor operatively associated therewith.

42. A method for determining the real-time $NO_2$ and NO content of the breathing gases of the breaths of a subject comprising the steps of:

providing a flow of breathing gases during the breaths of the subject through a sample chamber;

passing radiation from a semiconductor radiation source through the breathing gases in the sample chamber, said radiation having an emission spectrum with a maximum wavelength of about 600 nm;

operating the radiation source at a sampling frequency of at least about 10 Hz;

sensing the radiation exiting the breathing gases;

determining the $NO_2$ content of the breathing gases from the optical spectral absorption characteristics of the sensed radiation resulting from the presence and amount of $NO_2$ in the breathing gases in a response time of about 200 ms such that the $NO_2$ content of the gas sample can be determined in real-time with respect to the breaths of the subject; and passing breathing gas discharged from the sample chamber through an NO gas sensor providing real time measurement of the NO content of the breathing gases.

43. The method according to claim 42 further defined as passing radiation having an emission spectrum with a maximum wavelength of about 520 nm through the breathing gases.

44. The method according to claim 42 further defined as passing radiation having an emission spectrum with wavelengths in a range of about 380–520 nm through the breathing gases.

45. The method according to claim 42 further defined as passing radiation from a light emitting diode radiation source through the breathing gases.

46. The method according to claim 42 further defined as passing radiation from a laser diode through the breathing gases.

47. The method according to claim 42 further including the step of carrying out a filter sensing of the radiation exiting the breathing gases and using the results of said further sensing to provide compensation to said first mentioned sensing.

48. The method according to claim 47 wherein said further sensing is carried out under conditions of reduced sensitivity to spectral absorption resulting from the presence of $NO_2$ in the breathing gases.

49. The method according to claim 47 wherein said further sensing is carried out using a different spectral region of the emission spectrum than is employed in said first mentioned sensing.

50. The method according to claim 48 wherein said further sensing is carried out using a different emission spectrum than is used in said first mentioned sensing.

51. The method according to claim 42 further defined as sensing the temperature of the breathing gases and compensating the sensing results of said sensing step.

52. The method according to claim 51 further defined as heating the breathing gases.

53. The method according to claim 42 further defined as passing the breathing gases discharged from the sample chamber through a chemiluminescent NO gas sensor.

54. The method according to claim 42 further defined as passing the breathing gases discharged from the sample chamber through an electrochemical cell.

55. The method according to claim 42 further defined as operating the radiation source at a sampling frequency in the kHz range.

56. A method for real-time determination of the $NO_2$ content of the breathing gases of the breaths of a subject, said method comprising the steps of:

providing a flow of breathing gases during the breaths of the subject through a sample chamber;

passing radiation from a first semiconductor radiation source through the breathing gases in the sample chamber, said radiation from said first source having an emission spectrum with a maximum wavelength of about 600 nm;

passing radiation from a second semiconductor radiation source through the breathing gases in the sample chamber, the wavelength of the radiation from said second source being such as to minimize absorption of the radiation by nitrogen dioxide;

the first and second radiation sources being alternately operated at a selected sampling frequency;

sensing the radiation exiting the breathing gases as a result of the alternative operation of the radiation sources; and determining the $NO_2$ content of the breathing gases from the sensed exiting radiation in real-time with respect to the breaths of the subject.

57. The method according to claim 56 further defined as passing radiation from said first source having an emission spectrum with a maximum wavelength of about 520 nm.

58. The method according to claim 56 further defined as passing radiation from said first source having an emission spectrum with wavelengths in a range of about 380–520 nm.

59. The method according to claim 56 further defined as passing radiation from a light emitting diode radiation source through the breathing gases.

60. The method according to claim 56 further defined as passing radiation from a laser diode through the breathing gases.

61. The method according to claim 56 further defined as sensing the temperature of the breathing gases and compensating the sensing results of said sensing step.

62. The method according to claim 61 further defined as heating the breathing gases.

63. The method according to claim 56 further defined as operating each of the first and second radiation sources at a sampling frequency of at least about 10 Hz.

64. The method according to claim 63 further defined as operating the first and second radiation sources at a sampling frequency in the kHz range.

65. The method according to claim 56 further including the step of measuring the NO content of the breathing gases.

* * * * *